(12) United States Patent
Bani-Hashemi et al.

(10) Patent No.: US 6,839,405 B2
(45) Date of Patent: Jan. 4, 2005

(54) SYSTEM AND METHOD FOR ELECTRONIC SHAPING OF X-RAY BEAMS

(75) Inventors: Ali Bani-Hashemi, Walnut Creek, CA (US); Wolf Ekkehard Blanz, Danville, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 130 days.

(21) Appl. No.: 10/159,569

(22) Filed: May 31, 2002

(65) Prior Publication Data

US 2003/0223538 A1 Dec. 4, 2003

(51) Int. Cl.[7] .............................. A61N 5/10; H01J 35/30
(52) U.S. Cl. .......................... 378/65; 378/64; 378/119; 378/137
(58) Field of Search ............................ 378/64, 65, 84, 378/119, 121, 136, 137, 138

(56) References Cited

U.S. PATENT DOCUMENTS

| | | | |
|---|---|---|---|
| 1,865,441 A | | 7/1932 | Mutscheller |
| 2,557,662 A | | 6/1951 | Kirkpatrick .................. 250/53 |
| 2,638,554 A | | 5/1953 | MacLaughlin et al. |
| 4,426,722 A | | 1/1984 | Fujimura |
| 4,748,650 A | * | 5/1988 | Ammann ..................... 378/137 |
| 5,490,197 A | * | 2/1996 | Albert et al. ................ 378/113 |
| 5,497,008 A | * | 3/1996 | Kumakhov .............. 250/505.1 |
| 5,661,773 A | * | 8/1997 | Swerdloff et al. ............. 378/65 |
| 5,812,631 A | * | 9/1998 | Yan et al. ....................... 378/85 |
| 6,125,295 A | | 9/2000 | Cash, Jr. et al. ............. 600/431 |
| 6,134,296 A | | 10/2000 | Siochi |
| 6,195,410 B1 | | 2/2001 | Cash, Jr. ........................ 378/43 |
| 6,359,963 B1 | | 3/2002 | Cash ............................ 378/65 |
| 6,366,801 B1 | | 4/2002 | Cash, Jr. et al. ............. 600/431 |
| 2001/0043667 A1 | * | 11/2001 | Antonell et al. ............... 378/84 |

FOREIGN PATENT DOCUMENTS

| | | |
|---|---|---|
| DE | 100 60 888 A1 | 9/2001 |
| GB | 2 295 266 | 5/1996 |
| WO | WO 99/48558 | 9/1999 |

OTHER PUBLICATIONS

Minimizing Static Intensity Modulation Delivery Time Using An Intensity Solid Paradigm, R. Alfredo. Siochi, PHD., Int. J. Radiation Oncology Biol. Phys. vol. 43, No. 3, pp. 671–680, 1999.

Multilevel Collimator Leaf Sequencing Algorithm for Intensity Modulated Beams With Multiple Static Segments, Ping Xia and Lynn J. Verhey, Med. Phys. 25 (1998), 1424–1434.

Dynamic Multilevel Collimation Without "Tongue-and--groove"Underdosage Effects, J P C van Stanvoort and B J M Heijmen Pys. Med. Biol. 41 (1990) pp. 2091–2105, printed in the UK.

The Effect of Stair–Step Leaf Transmission on the "Tongue--and–Groove Problem"in Dynamic Radiotherapy with a Multileaf Collimator, Phys. Med. Biol. 42 (1997) 595–602, printed in the UK.

Configuration Options for Intensity–Modulated Radiation Therapy Using Multiple Static Fields Shaped by a Multileaf Collimator. II. Constituents and Limitations on 2D Modulation, Phys. Med. Biol. 43 (1998) 24181–1495, printed in the UK.

* cited by examiner

*Primary Examiner*—Edward J. Glick
*Assistant Examiner*—Allen C. Ho

(57) ABSTRACT

A system and method for delivering radiation that comprises a source for creating an electron beam, a system that focuses the electron beam and then deflects the beam such that the beam is swept across a first target as an arbitrary pattern. The arbitrary pattern on the first target is given an additional intensity modulation. Thereafter, a lens focuses the arbitrary pattern of electrons from the first target onto a second target.

12 Claims, 4 Drawing Sheets

SYSTEM AND METHOD FOR ELECTRONIC SHAPING OF X-RAY BEAMS

BACKGROUND OF THE INVENTION

Focused X-ray beams have shown a promising future in low-energy external beam radiation therapy. The development of X-ray lenses for diagnostic X-ray energy levels ($\approx$100 keV) enables the use of external beam radiotherapy at these energies. Like conventional high-energy beam therapy, the shaping of the beam is a concern.

An X-ray lens may focus X-ray beams for delivery to a target, while minimizing the dose delivered to the tissues along the beams' path. FIG. 1 illustrates how a target inside a patient is radiated with an X-Ray cone. The intersection of the patient's skin and the X-Ray cone is a larger area than the area of the target. Hence, the energy per unit area (dose) is smaller outside the target area, in particular at the skin. This is due to the cone geometry of the lens system.

X-ray lenses image an X-ray source from an anode (the electron focal point) onto a focal plane. The X-ray lens's deflection of the x-ray beams is similar to an optical lens's deflection of visible light. The image on the anode is produced by the X-ray lens onto the focal plane (FIG. 2). Due to the physical limitations, as well as the characteristics of the focusing system (lens), the image of an ideal point source at the focal plane will not be a point. The image of such a point source will be determined by the characteristic function of the optics and will be represented by the system's Point Spread Function (PSF). The PSF together with the actual shape of the focal point of the electrons on the X-ray anode, which is also of finite extension, determines the size and the shape of the X-Ray focus at the focal plane. In general, the x-ray focal spot will not match the size and the shape of the target that is to be radiated, but will be considerably smaller than the target.

To remedy this problem, one solution is for the overall X-Ray system (source and the lens) to sweep the target in order to create the needed coverage. This kind of sweeping involves mechanical movement of the overall X-Ray system, such as a robotic arm. Alternatively, an MLC/port type device may shape a broad beam by electromechanical methods, but such a method is slow and unreliable. In order to create a needed flux pattern at the target, i.e. a dose distribution over the target, there is a need for multiple exposure patterns created by several overlapping sweepings.

SUMMARY OF THE INVENTION

A desired dose is delivered to the target by changing the shape of the beam to match the shape of the target and a dose distribution is created that matches the desired profile at the target.

A system and method for delivering radiation that comprises a source for creating an electron beam, a system that focuses the electron beam and then deflects the beam such that the beam is swept across a first target as an arbitrary pattern. The arbitrary pattern on the first target is given an additional intensity modulation. Thereafter, a lens focuses the arbitrary pattern of electrons from the first target onto a second target.

DETAILED DESCRIPTION

The following description is presented to enable one of ordinary skill in the art to make and use the invention. Descriptions of specific embodiments and applications are provided only as examples and various modifications will be readily apparent to those skilled in the art. The general principles described herein may be applied to other embodiments and applications without departing from the scope of the invention. Thus, the present invention is not to be limited to the embodiments shown, but is to be accorded the widest scope consistent with the principles and features described herein. For purpose of clarity, details relating to technical material that is known in the technical fields related to the invention have not been described in detail.

Figure 1:
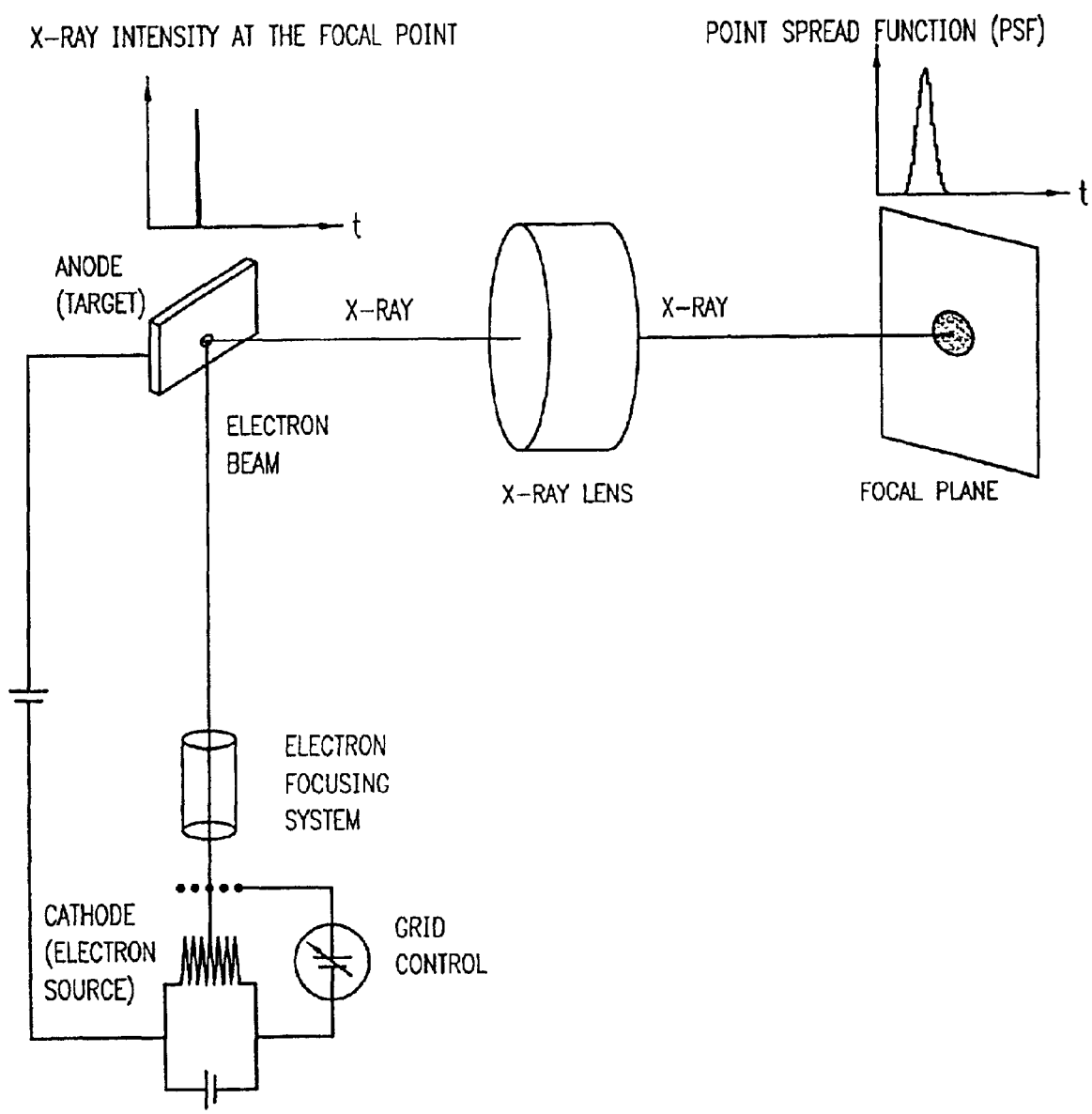
FIG. 1 is a diagram illustrating the use of an x-rays lens to irradiate a targeted area of a patient.
Figure 2:
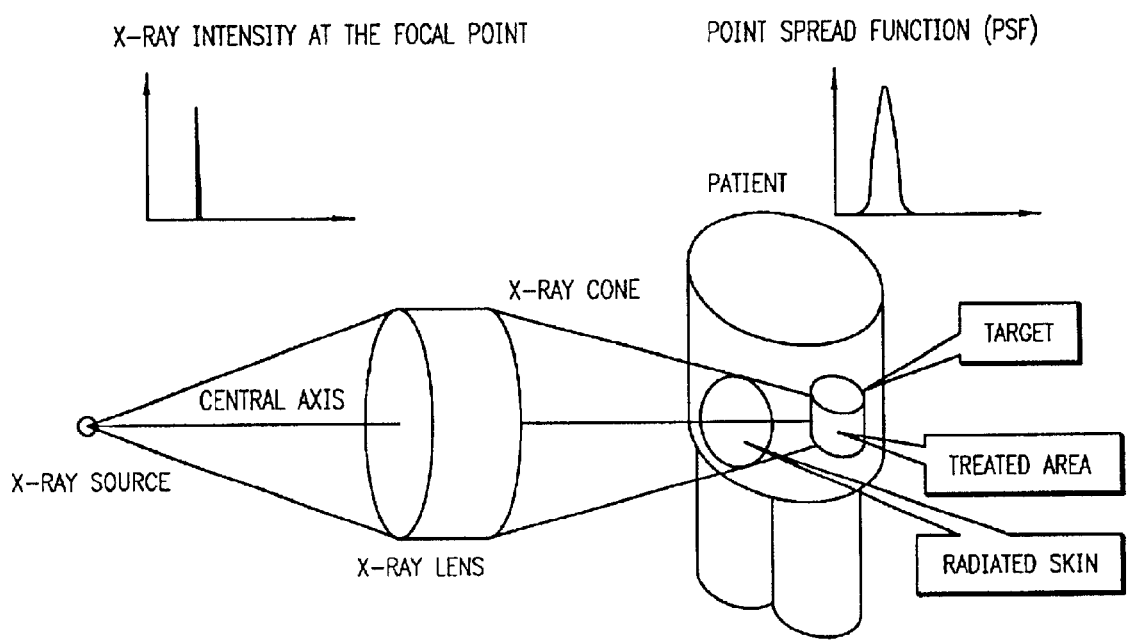
FIG. 2 is a diagram illustrating the prior art usage of an x-ray lens to focus a focal point into a focal plane.
Figure 3:
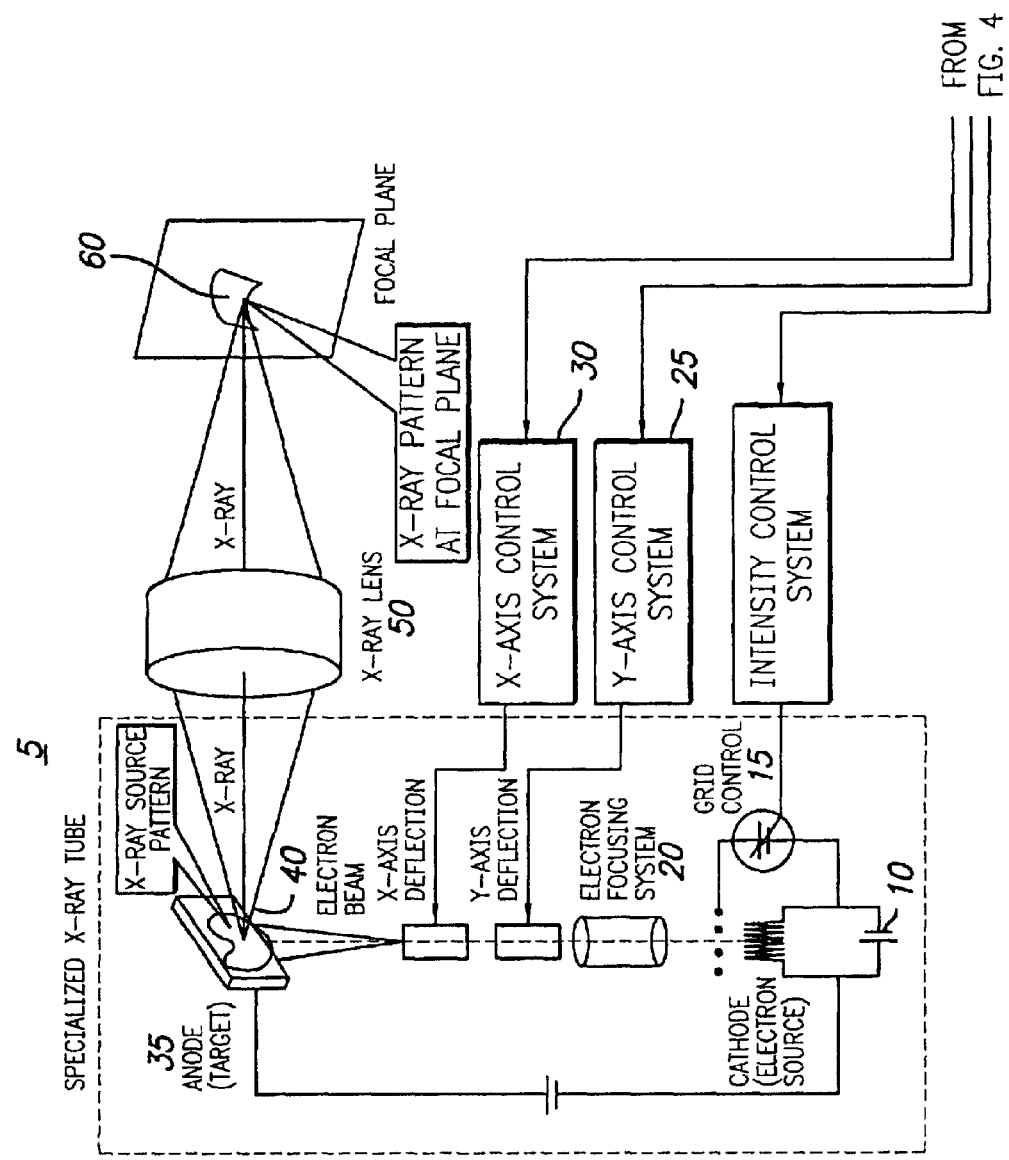
FIG. 3 is a diagram illustrating an x-ray tube and lens system according to some embodiments of the present invention.

FIG. 3 illustrates the basic design of an X-ray tube 5 for creating an arbitrarily-shaped X-ray beam. Cathode 10 emits the electrons, and grid control 15 controls the intensity profile of the x-ray source (the electrons). Electron focusing system 20 creates an electron beam. A computer program sends the values corresponding to the amount of X-axis and Y-axis deflections to the Y-axis control stem 25 and to the X-axis control system, and directs control system 25 and 30 to generate X-axis and Y-axis deflection signals that match the shape of the target 60, taking into consideration the particular characteristics of X-ray lens 50, such as the PSF and the lens shape transformation. The X-axis and Y-axis deflections of the electron beam cause the beam to sweep across anode 35 and create an x-ray source pattern 40. The anode 35 is positively charged to attract the deflected electron beam. The intensity of the electron beam (current) is controlled for example, such that x-ray source pattern 40 is given additional intensity modulation. The desired X-ray beam shape and intensity profile at the target are back-projected through the X-ray lens system to the X-ray source. In other words, the computer determines the geometric shape and intensity profile of the X-ray source that should result in the desired shape and intensity profile at the target (i.e. the lesion under treatment). This is known as inverse-filtering.

Accordingly, with these three control signals: (1) the x-axis deflection signal, (2), the y-axis deflection signal, and (3) the signal related to the intensity of x-ray source), an electron image is created at anode 35. This may be similar to a CRT tube technology used in tube-based televisions, except that the sweeping is not a strictly rectangular, but arbitrarily shaped area. X-rays are irradiated from the area of the x-ray source pattern 40 onto x-ray lens 50. One example of an X-ray tube with electromagnetic deflection, exists as a prototype and is manufactured by Siemens.

X-ray lens 50 is made of X-ray deflecting material, such as, but not limited to, silicon or graphite, and images the X-ray source pattern 40 onto target 60. Due to the PSF of the (lens) focusing system, the shape at target 60 will not be identical to the shape of X-ray source pattern 40. Thus, the focusing system PSF inverse-filters the desired target shape and fluence map to obtain the ideal image at the X-Ray source pattern 40. Due to the characteristics of the lens, the desired pattern at the target will not be identical to the pattern at the X-ray source. In some situations, the desired beam shape and profile may not be achievable. In this case, an acceptable approximation must be made. For example, a target shape with an abrupt intensity change (i.e. infinite gradient) is not known to be achievable with any causal/practical system.

Figure 4:
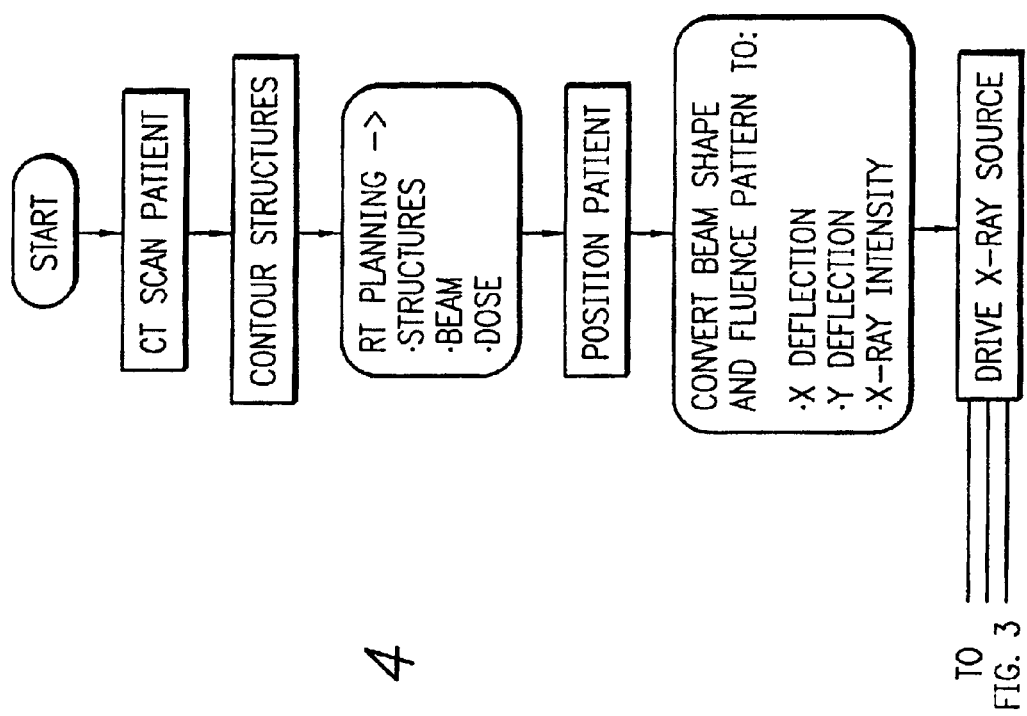
FIG. 4 is a diagram illustrating the process of using the system according to some embodiments of the present invention.

FIG. 4 depicts the steps of an embodiment of a treatment scenario. First, the patient is computed tomography (CT) scanned for treatment planning, and the target and critical structures are delineated, as is normally performed. Additionally, the treatment planning creates a fluence map that determines the quantity of x-ray radiation (either particle fluence, the number of photons entering a sphere of unit cross-sectional area, or energy fluence, the sum of the energies of the photons passing through a unit area) for different portions of the target.

In a typical radiation therapy planning system, the information from the CT is used to create beams to optimize the dose distribution to the target and avoid critical structures. The patient is positioned for delivery (similar to conventional treatment), and the beam's shape and intensity are inverse filtered to compensate for the particular characteristics of the X-Ray focusing system. Next, the signals for the X-axis deflection, Y-axis deflection, and X-ray intensity of the electron beam are calculated using a computer program. These signals drive the electron beam, which in turn creates an X-Ray beam.

Although the present invention has been described in accordance with the embodiments shown, one of ordinary skill in the art will readily recognize that there could be variations to the embodiment and these variations would be within the spirit and scope of the present invention. Accordingly, many modifications may be made by one of ordinary skill in the art without departing from the spirit and scope of the appended claims.

What is claimed is:

1. A system for delivering radiation, the system comprising:

an X-ray tube having an electronic means for creating an X-ray source pattern on a first target;

a radiation focusing system that focuses an X-ray beam irradiated from the X-ray source pattern onto a second target in a desired shape; and a computer to determine the X-ray source pattern by inverse-filtering the desired shape to compensate for characteristics of the radiation focusing system.

2. The system of claim 1 wherein the means for creating an X-ray source pattern on a first target is a system that controls the deflection of an electron beam.

3. The system of claim 1 wherein the X-ray source pattern received on the first target is not a point.

4. A system for delivering radiation, the system comprising:

a source for creating an electron beam;

means for focusing the electron beam;

means for deflecting the electron beam, such that the electron beam is swept across a first target in an X-ray source pattern;

means for modulating an intensity of the X-ray source pattern on the first target;

a radiation focusing system that focuses an X-ray beam irradiated from the X-ray source pattern of the first target onto a second target in a desired shape; and a computer to determine the X-ray source pattern by inverse-filtering the desired shape to compensate for characteristics of the radiation focusing system.

5. The system of claim 4, wherein the first target is a positively charged anode.

6. The system of claim 4, further comprising a grid that controls the intensity of the electron beam source.

7. The system of claim 4, wherein the means for deflecting the electron beam deflects the x-axis of the electron beam.

8. The system of claim 4, wherein the means for deflecting the electron beam deflects the y-axis of the electron beam.

9. A method of delivering radiation, the method comprising the steps:

determining an electron source pattern by inverse-filtering a desired electron beam shape to compensate for characteristics of a radiation-focusing system;

electronically creating the X-ray source pattern on a first target with an electron source; and focusing on X-ray beam irradiated from the X-ray source pattern onto a second target in the desired shape using the radiation focusing system.

10. A method of delivering radiation, the method comprising the steps: determining a shape of an X-ray beam for delivering radiotherapy to targeted structures of an object;

inverse filtering shape of the X-ray beam to compensate for the-characteristics of an X-ray focusing system;

calculating x-axis deflection and y-ray deflection signals based on the inverse-filtered X-ray beam shape;

using the x-axis deflection and y-axis deflection signals to focus an electron beam onto an anode in an source pattern; and using the X-ray focusing system to focus an X-ray beam irradiated from the X-ray source pattern onto the targeted structures of the object.

11. The method of claim 10 wherein the X-ray focusing system comprises a lens.

12. The method of claim 10, further comprising:

determining an intensity of the X-ray beam for delivering radiotherapy to the target structures of the object;

inverse filtering the intensity of the X-ray beam to compensate for the characteristics of the X-ray focusing system;

calculating an X-ray intensity signal based on the inverse-filtered X-ray beam intensity; and using the X-ray intensity signal to control an intensity of the electron beam focused onto the anode in the X-ray source pattern.

* * * * *